United States Patent [19]
Wiegert

[11] 3,953,497

[45] Apr. 27, 1976

[54] 2,4,6-TRIIODO-5-METHOXYACETAMIDO-N-METHYLISOPHTHALAMIC ACID AND SALTS, ACYL HALIDES AND ESTERS THEREOF

[75] Inventor: Philip E. Wiegert, St. Louis, Mo.

[73] Assignee: Mallinckrodt, Inc., St. Louis, Mo.

[22] Filed: July 29, 1974

[21] Appl. No.: 492,568

[52] U.S. Cl. .................. 260/471 R; 260/501.11; 260/519; 260/544 N; 424/5
[51] Int. Cl.² ..................................... C07C 103/76
[58] Field of Search ...... 260/471 R, 544 M, 501.11, 260/519

[56] References Cited
UNITED STATES PATENTS 3,666,800    5/1972    Bernstein et al. .............. 260/471 R

OTHER PUBLICATIONS

Klieger et al., Arch. Pharmaz., 306, (1973), pp. 834–845.

*Primary Examiner*—Richard L. Raymond
*Attorney, Agent, or Firm*—Mathew D. Madsen

[57] ABSTRACT

2,4,6-Triiodo-5-methoxyacetamido-N-methylisophthalamic acid and salts and esters thereof are useful as x-ray contrast agents. The corresponding acyl halides are useful as intermediates.

7 Claims, No Drawings

2,4,6-TRIIODO-5-METHOXYACETAMIDO-N-METHYLISOPHTHALAMIC ACID AND SALTS, ACYL HALIDES AND ESTERS THEREOF

BACKGROUND OF THE INVENTION

This invention relates to the field of organic chemistry, and more particularly to 2,4,6-triiodo-5-methoxyacetamido-N-methylisophthalamic acid and certain salts, acyl halides and esters thereof. These compounds are useful as x-ray contrast agents.

G.B. Hoey (U.S. Pat. No. 3,145,197/1964) disclosed 5-acetamido-2,4,6-triiodo-N-methylisophthalamic acid and its salts and their utility as components of aqueous x-ray contrast media. Subsequently, the coined terms "iothalamic acid" and "iothalamate" were applied to these compounds. A profuse literature relating to the radiological uses of these compounds has been published in succeeding years.

H. Priewe et al. of Schering AG (DAS 1,129,260/1962) disclosed the preparation of 3-acetamido-5-methoxyacetamido-2,4,6-triiodobenzoic acid and proposed its use as an x-ray contrast agent. They reported this compound as having an $LD_{50}$ (i.v. in rats) of 16 g/kg.

Subsequently, H. Pfeiffer et al., also of Schering AG (DOS 2,118,219/1972), reported that, notwithstanding the favorable toxicity data in rats, this compound causes strong circulatory disturbances in dogs and man. The use, as x-ray contrast media, of aqueous solutions of salts of various 2,4,6-triiodoisophthalamic and other 2,4,6-triiodobenzoic acids with pharmaceutically acceptable cations, e.g., sodium, calcium, magnesium and alkanolamines, such as ethanolamine, diethanolamine and meglumine (N-methylglucamine), is well known to those skilled in the art.

SUMMARY OF THE INVENTION

Among the objects of the invention may be mentioned the provision of new isophthalamic acid derivatives; the provision of new 2,4,6-triiodoisophthalamic acid compounds; the provision of compounds of the type indicated which are useful for the preparation of roentgenographic contrast media; and the provision of methods of preparing such compounds. Other objects will be in part apparent and in part pointed out hereinafter.

The present invention is directed to 2,4,6-triiodo-5-methoxyacetamido-N-methylisophthalamic acid and salts and acyl halides and ester derivatives thereof. The salts of the acid with pharmaceutically acceptable cations are useful in the preparation of x-ray contrast media intended primarily for intravascular administration. Other salts, such as ammonium salts, are useful as intermediates. Esters of the acid are useful in x-ray contrast media intended primarily for use in instillation procedures. Acyl halide derivatives of the acid are useful as intermediates for the preparation of amides and other non-ionic derivatives. In a preferred method, 5-amino-2,4,6-triiodo-N-methylisophthalamic acid is acylated by reaction with methoxyacetyl chloride, which may be generated in situ by treating methoxyacetic acid with thionyl chloride. The acylation reaction is carried out utilizing a polar aprotic solvent, preferably N,N-dimethylacetamide, as a reaction medium. Other polar aprotic solvents that may be utilized include dimethylformamide, N-methylpyrrolidone, etc.

Alternatively, the acid of the invention may be prepared as follows:

5-Amino-2,4,6-triiodo-N-methylisophthalamic acid is treated with an haloacetyl halide, such as bromoacetyl chloride or chloroacetyl chloride, in N,N-dimethylacetamide to give a 5-haloacetamido-2,4,6-triiodo-N-methylisophthalamic acid. The solvent is removed and the product is treated with sodium methoxide in methanol to provide 2,4,6-triiodo-5-methoxyacetamido-N-methylisophthalamic acid.

2,4,6-Triiodo-5-methoxyacetamido-N-methylisophthalamoyl chloride or other acyl halides of the invention may be made by the following general method. 2,4,6-Triiodo-5-methoxyacetamido-N-methylisophthalamic acid is treated with excess thionyl halide in N,N-dimethylacetamide. After removing the unreacted thionyl halide by evaporation under reduced pressure, the product is suitable for use as an intermediate in situ. Alternatively, the product is isolated by evaporating the solvent under vacuum.

The lower alkyl 2,4,6-triiodo-5-methoxyacetamido-N-methylisophthalamates of the invention may be prepared by the following general method. A 2,4,6-triiodo-5-methoxyacetamido-N-methylisophthalamoyl halide is treated with excess anhydrous lower alkanol in N,N-dimethylacetamide in the presence of potassium carbonate. After the reaction is complete, the reaction mixture is filtered to remove the inorganic salts and the lower alkyl 2,4,6-triiodo-5-methoxyacetamido-N-methylisophthalamate is isolated by evaporating the excess alcohol and the solvent.

EXAMPLE 1

A solution of methoxyacetyl chloride in N,N-dimethylacetamide was prepared by adding thionyl chloride (41.76 g., 0.36 mole) dropwise, with stirring, to a cooled solution of methoxyacetic acid (32.4 g., 0.36 mole) in N,N-dimethylacetamide (150 ml.) at such a rate that the temperature of the reaction mixture was maintained at 0–10°C. After the addition the solution was stirred at 0–5°C. for one hour. To this solution of methoxyacetyl chloride (at 0–8°C.) was added, in portions, a slurry of 5-amino-2,4,6-triiodo-N-methylisophthalamic acid (85.8 g., 0.15 mole) in N,N-dimethylacetamide (150 ml.).

After the addition of the slurry, the reaction mixture was stirred at 0–5° for 2 hours after which the temperature was raised to 25–30°. When the reaction mixture reached room temperature, a clear solution was obtained, and was allowed to stand overnight.

Water (90 ml.) was added to the solution with cooling (solution temperature below 25°) and the solution was stirred for 30 min. Water and N,N-dimethylacetamide were evaporated under vacuum, leaving a white solid residue. The product was slurried in water (100 ml.) and 2N $NH_4OH$ (500 ml.) was added, followed by 50% NaOH (about 10 ml.) until a clear solution was obtained. The solution was filtered and was then added dropwise to a stirring mixture of water (500 ml.) and sulfuric acid (100 ml.) with cooling. The resulting precipitate of 2,4,6-triiodo-5-methoxyacetamido-N-methylisophthalamic acid was collected and dried. Yield, 90 g. (93%). Examination by TLC with two systems ethyl acetate:methanol:acetic acid (10:5:1) and isobutyl alcohol:isopropyl alcohol:ammonium hydroxide (28% $NH_3$) (10:4:4) showed a single spot in each case. IR and NMR spectra are in agreement with the postulated structure.

An analytical sample was further purified by preparing a solution of the sodium salt, adding this solution dropwise to a cold stirred solution of 'N hydrochloric acid, slurrying the precipitated free acid in water, collecting the acid and drying it.

Anal. Calc'd. for $C_{12}H_{11}I_3N_2O_5$: C, 22.38%; H, 1.72%; I, 59.12%; N, 4.35%; N.E., 643.93. Found: C, 22.08%; H, 1.80%; I, 58.90%; N, 4.27%; N.E., 648.61; M.P. 285.8–287.8°C. (dec.).

EXAMPLE 2

2,4,6-Triiodo-5-methoxyacetamido-N-methylisophthalamic acid (6.005 g.) was dissolved in water with NaOH solution at pH 7.4 to form a supersaturated solution (7.0 ml.). When the solution was allowed to stand at room temperature overnight, crystallization occurred. The crystals were collected and dried.

The sodium salt (2.71 g.) was then dissolved in water to form an 82% w/v solution (3.3 ml.). After the solution was allowed to stand at 24° overnight some crystallization occurred. The solution was stirred and the supernatant was taken (by centrifugation) for specific gravity measurement (sp. gr. 1.43) and for water determination (found, 49.7% w/v by Karl Fischer method). The solubility of the sodium salt in water was therefore determined to be about 70% w/v at 24°. The solubility is highly temperature dependent.

EXAMPLE 3

2,4,6-Triiodo-5-methoxyacetamido-N-methylisophthalamoyl chloride

A solution of 2,4,6-triiodo-5-methoxyacetamido-N-methylisophthalamic acid in N,N-dimethylacetamide is treated with an excess of thionyl chloride. After the reaction, the excess thionyl chloride is removed by evaporation and the product is suitable for use as intermediate in situ.

EXAMPLE 4

Ethyl 2,4,6-triiodo-5-methoxyacetamido-N-methylisophthalamate

A solution of 2,4,6-triiodo-5-methoxyacetamido-N-methylisophthalamoyl chloride in N,N-dimethylacetamide (prepared as in Example 3) is treated with absolute ethanol in the presence of potassium carbonate. After the reaction is complete, the inorganic salts are removed by filtration and the filtrate is evaporated to dryness to provide ethyl 2,4,6-triiodo-5-methoxyacetamido-N-methylisophthalamate.

EXAMPLE 5

A buffered stabilized solution of sodium 2,4,6-triiodo-5-methoxyacetamido-N-methylisophthalamate is prepared by adding with stirring, sufficient sodium hydroxide pellets to a slurry of 2,4,6-triiodo-5-methoxyacetamido-N-methylisophthalamic acid (494 g.) in water (650 ml.) to dissolve the acid and provide a neutral to faintly acid solution, adding calcium disodium edetate (400 mg.), trisodium citrate dihydrate (2.47 g.), adjusting the pH to the range 6–7, if necessary, by titration with 5 N sodium hydroxide solution, diluting the solution to about 900–950 ml., titrating to pH 7.4 with 0.1 N sodium hydroxide, and finally adjusting the volume to exactly 1000 ml. The resulting solution, containing 292 mg. iodine per milliliter is subdivided into vials and is sterilized by autoclaving.

EXAMPLE 6

A buffered, stabilized solution of meglumine 2,4,6-triiodo-5-methoxyacetamido-N-methylisophthalamate is prepared by stirring sufficient meglumine (N-methylglucamine) into a slurry of 2,4,6-triiodo-5-methoxyacetamido-N-methylisophthalamic acid (338 g.) in water (250 ml.) to dissolve the acid and provide neutral to faintly acid solution, adding calcium disodium edetate (55 mg.), making the solution faintly alkaline (pH 7.4) by the careful addition of a solution of meglumine, adding sodium dihydrogen phosphate (70 mg.) with stirring, readjusting the pH to 7.4 and diluting the solution to 500 ml. The resulting solution, containing 400 mg. of iodine per milliliter, is subdivided into vials and is sterilized by autoclaving.

EXAMPLE 7

To a stirred slurry of 592 g. of 2,4,6-triiodo-5-methoxyacetamido-N-methylisophthalamic acid in 600 ml. of water are added at 55°C., 1.03 g. of magnesium chloride hexahydrate, 2.31 g. of calcium chloride dihydrate, 20 g. of sodium hydroxide pellets, 52.2 g. of N-methylglucamine, 110 mg. of calcium disodium edetate, and 125 mg. of sodium dihydrogen phosphate. The formulation is then adjusted to pH 7.4 using a solution of 7.8 g. of N-methylglucamine and 3 g. of sodium hydroxide in 50 ml. of water. The pH adjustments are effected under a nitrogen atmosphere. After diluting to a final volume of a little less than 1,000 ml., the solution is stirred under nitrogen overnight at room temperature, readjusted to pH 7.4 the next day, and diluted to a final volume of 1,000 ml. This formulation contains 350 mg. iodine per milliliter. It is subdivided into ampuls and sterilized by autoclaving.

Satisfactory intravenous urograms are obtained when any of the preparations described in Examples 5–7 is administered to dogs at a dosage of 350 mg. I/kg.

Toxicity evaluations by three different techniques were carried out on solutions of the meglumine salts of the 2,4,6-triiodo-5-methoxyacetamido-N-methylisophthalamic acid of the invention and of the known compound iothalamic acid. The techniques utilized are outlined below.

I. Acute Intravenous Toxicity Studies in Mice

Swiss Albino mice (Charles River) were dosed in the lateral tail vein with solutions of the iodinated compound containing 28.27% of iodine, injected at the rate of 1 ml/min. Following injections the animals were observed for immediate reactions and then daily throughout a seven day observation period. The $LD_{50}$ values were calculated by the method of Litchfield and Wilcoxon (J. of Pharmac. and Exptl. Therap. 96:99–113, 1949).

II. Intracerebral Toxicity in Mice

Swiss Albino mice (Charles River) were used. Fixed volumes of solutions of various concentrations of the iodinated compounds were injected intracerebrally via a 27 gauge needle, (¼ inch length) according to the method of Haley, et al. (Br. J. of Pharmac. 12:12–15, 1957). The animals were observed immediately after injections and daily throughout a seven day observation period. The $LD_{50}$ values were calculated by the method of Litchfield and Wilcoxon (J. of Pharmac. and Exptl. Therap. 96:99–113, (1949).

III. Intracisternal Toxicity in Rats

Sprague Dawley (Carworth) rats were used. The method used is a variation of the procedure outlined by Melartin et al. (Invest. Rad. 5:13–21, 1970). After dosing, the animals were housed individually, and observed for immediate reactions and periodically for a two day observation period. The $LD_{50}$ values were calculated according to the method of Litchfield and Wilcoxon, (J. of Pharmac. and Exptl. Therap. 96:99–115, 1949).

The results of these toxicity evaluations are set forth in Table 1.

Table 1

Toxicity Values for Meglumine Salts of
2,4,6-Triiodo-5-Methoxyacetamido-N-Methyl-
isophthalamic Acid and Iothalamic Acid

| Acid | $LD_{50}$ of Meglumine Salt* | | |
|---|---|---|---|
| | I.V. (Mice) | Intracerebral (Mice) | Intracisternal (Rats) |
| 2,4,6-Triiodo-5-Methoxyacetamido-N-methylisophtha-amic Acid | 6700 | 700 | 40 |
| Iothalamic Acid | 5742 | 280 | 86 |

*All $LD_{50}$ values are expressed in terms of mg. contained iodine/kg. animal body weight.

The impressive IV $LD_{50}$ value for the meglumine salt of 2,4,6-triiodo-5-methoxyacetamido-N-methylisophthalamic acid suggests that this and other non-toxic water soluble salts of this acid would be superior x-ray contrast agents for intravenous urography and other intravascular roentgenographic procedures.

In view of the above, it will be seen that the several objects of the invention are achieved and other advantageous results obtained.

As various changes could be made in the above products and methods without departing from the scope of the invention, it is intended that all matter contained in the above description shall be interpreted as illustrative and not in a limiting sense.

What is claimed is:

1. A compound selected from the group consisting of 2,4,6-triiodo-5-methoxyacetamido-N-methylisophthalamic acid, the ammonium salt thereof, salts thereof with pharmaceutically acceptable cations, lower alkyl esters thereof, and the acyl halide thereof.

2. A compound as defined by claim 1 which is 2,4,6-triiodo-5-methoxyacetamido-N-methylisophthalamic acid.

3. A compound as defined by claim 1 which is a salt of 2,4,6-triiodo-5-methoxyacetamido-N-methylisophthalamic acid with a pharmaceutically acceptable cation.

4. A compound as defined by claim 3 wherein the pharmaceutically acceptable cation is sodium.

5. A compound as defined by claim 3 wherein the pharmaceutically acceptable cation is meglumine.

6. A compound as defined by claim 1 which is 2,4,6-triiodo-5-methoxyacetamido-N-methylisophthalamoyl chloride.

7. A compound as defined by claim 1 which is ethyl 2,4,6-triiodo-5-methoxyacetamido-N-methylisophthalamate.

* * * * *